United States Patent [19]
Häsing et al.

[11] Patent Number: 5,938,605
[45] Date of Patent: *Aug. 17, 1999

[54] MEASURING PROCESS AND SENSOR FOR ON-LINE IN-VIVO DETERMINATION OF THE TISSUE-EQUIVALENT DOSE IN RADIOTHERAPY

[75] Inventors: Friedrich-Wolfgang Häsing; Harald Büker, both of Jülich, Germany

[73] Assignee: Forschungszentrum Julich GmbH, Julich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/894,568
[22] PCT Filed: Feb. 1, 1996
[86] PCT No.: PCT/DE96/00174
§ 371 Date: Aug. 6, 1997
§ 102(e) Date: Aug. 6, 1997
[87] PCT Pub. No.: WO96/24859
PCT Pub. Date: Aug. 15, 1996

[30] Foreign Application Priority Data

Feb. 6, 1995 [DE] Germany ............ 195 03 647

[51] Int. Cl.⁶ .................................................. A61B 6/00
[52] U.S. Cl. ......................... 600/436; 250/370.07
[58] Field of Search ................... 600/431, 436, 600/1, 3; 250/370.07

[56] References Cited

U.S. PATENT DOCUMENTS 5,014,708  5/1991  Hayashi et al. .

FOREIGN PATENT DOCUMENTS 0 103 835 A2  3/1984  European Pat. Off. .
0 416 493 A3  3/1991  European Pat. Off. .
0 608 101 A3  7/1994  European Pat. Off. .

OTHER PUBLICATIONS

"Fiber–Optic Radiation Dosimetry for Medical Applications" by Bueker et al., SPIE vol. 1201 Optical Fibers V(1990).
"Physical properties and concepts for applications of attenuation–based fiber optic dosimeters for medical instrumentation" by Bueker et al. SPIE vol. 1648 (1992).
A Tissue Equivalent Semiconductor Detector for In–Vivo Dosimetry by G. Jacob et al. (Nuclear Instruments and Methods 101 (1972) North–Holland Publications.

Primary Examiner—Ruth S. Smith
Attorney, Agent, or Firm—Herbert Dubno

[57] ABSTRACT

A process and measuring device for determining the tissue-equivalent dose in radiotherapy. First, the radiation dose is measured according to the process at a site by at least two sensors i and j. The sensors are designed such that the associated measuring signals $S_i$ and $S_j$ display different energy dependency of the detection sensitivity to ionizing radiation, a dose-independent quotient $Q_{ij}=S_i/S_j$ being formed from this difference. The tissue-equivalent dose D is then calculated from this dose-independent value. The advantages of this process are that the sensor material does not have to be adapted to the tissue and can therefore be freely selected, and the tissue-equivalent dose is determined highly accurately. The measuring device comprises three parallel fiber-optic sensors disposed equidistant in a plane, the outer sensors being identical and differing from the central sensor by differing energy dependency of the detection sensitivity to ionizing radiation.

3 Claims, 9 Drawing Sheets

MEASURING PROCESS AND SENSOR FOR ON-LINE IN-VIVO DETERMINATION OF THE TISSUE-EQUIVALENT DOSE IN RADIOTHERAPY

CROSS REFERENCE TO RELATED APPLICATIONS

This application is a national phase of PCT/DE96/00174 filed Feb. 1, 1996 and based, in turn, upon German national application 195 03 647.6 filed Feb. 6, 1995.

FIELD OF THE INVENTION

The invention relates to a process for the in-vivo and on-line determination of the tissue equivalent dose in radiotherapy as well as to a device for carrying out the process.

BACKGROUND OF THE INVENTION

It is known to carry out an in-vivo measurement of an approximate tissue equivalent dose with miniaturized thermoluminescence dosimeters in certain applications. A drawback, however, is this limitation to certain applications. In addition, the measurement results are only available after expensive evaluation of the thermoluminescense dosimeter at the earliest an hour after termination of the irradiation.

Furthermore, there are numerous proposals and investigations into fiberoptic measurements of the dose or, using semiconductor dosimeters in-vivo and on-line (U.S. Pat. No. 5,014,708 of May, 1991; H. Büker et al, Fiber-Optic Radiation Dosimetrie for Medical Application, SPIE, Vol. 1201, Optical Fibers in Medicine V. P. 419–429(1990); H. Büker et al., Physical Properties and Concepts for Applications of Attenuation-based Fiber-Optic Dosimeters for Medical Instrumentation, SPIE, Vol. 1648, Fiber Optic Medical and Fluorescent Sensors and Applications, P. 63–70(1992)).

According to the proposals and investigations, sensors are used whose material has an effective atomic number significantly deviating from the tissue or a reduced sensitivity. It is, however, a drawback that a precise measurement, especially in the case of photon radiation, is not possible since the material of the sensor always deviates from that of the tissue and the absorbed dose is material dependent. Further, the information regarding the tissue depth is not in principle available. It is therefore a drawback that the choice of material is limited.

OBJECT OF THE INVENTION

It is the object of the invention to overcome the indicated drawbacks by providing a measurement process and device for carrying out the process which enables on-line and in-vivo determination of the tissue equivalent dose in radiotherapy.

SUMMARY OF THE INVENTION

This object is achieved as follows:

In detail, the process can be carried out as follows:

A radiation dosage is measured by at least two sensors with an energy-dependency differing from one another for ionizing radiation and at least one quotient is formed from the measuring signals obtained from the sensors. That quotient is used to derive the tissue equivalent dosage.

Initially the radiation dose at a location is measured by at least two sensors. The sensors are so selected that within the measurement range the radiation dose varies in proportion to the measurement signal. It is sufficient in this case to determine by a compensating calculation the proportionality between the measurement signal and the radiation dose.

At least two measured signals $S_i$ and $S_j$ of the sensors i and j used must show an energy dependency of the detection sensitivity for ionizing radiation differing from one another. Such a difference in dependency is obtained with optical sensors with different effective atomic numbers $Z_{eff}$. The different indications can however also be achieved by a different shielding of each of the sensors.

At least one quotient $Q_{ij}=S_i/S_j$ between, measured signals $S_i$ and $S_j$ of these sensors i and j is formed. One signal $S_i$ can be obtained from one of the sensors i or j or as a mean value of a number of measurement signals from a plurality of sensors used, which has the same dependency on the detection sensitivity for ionizing radiation. It is decisive that a value dependent on the dose be used for the further evaluation. As an alternative to simple quotient formation, quotients like $(S_i-S_j)/(S_i+S_j)$ or their inverses can be used. In the description below, the simple quotient formation $Q_{ij}$ is used.

Further the effective tissue depth $d_g$ associated with the calculated quotient $Q_{ij}$ is obtained. This is achieved based upon calibration tables or calibration curves. The requisite data for generating these tables or curves are obtained by calibration measurements of a dose distribution in dependence upon the geometry depth $d_g$, in a phantom, for example, in a water bath or a PMMA (polymethylmethacrylate) phantom. This geometric depth $d_g$ is designated as the effective tissue depth since the geometric depth during the measurement basically deviates from the depth during the calibration measurement. From the determined effective tissue depth $d_g$, the calibration factors depend upon $d_g$, $K_i(d_g)$ and $K_j(d_g)$ of the sensors $S_i$ and $S_j$ are determined. The calibration factors can be determined experimentally in the phantoms with respect to an ionization chamber in a depth dependency $S_i(d_g)=K_i(d_g)*D$.

$$D = \left(\sum_{i=1}^{N} K_i(d_g)*S_i\right)/N$$

can then be calculated where N is the number of the calibration factor, dg is the function variable, Si is the sensor signal dependent on that variable and $K_i$ is a constant which is also a function of that variable. In the case of the sensors $S_1$ and $S_2$ this reduces to $D=(K_1(d_g)*S_1+K_2(d_g)*S_2)/2$.

The advantages of the invention are: the material of the sensor need not be matched to the tissue and can be freely chosen. The tissue equivalent dose is calculated extremely accurately. Apart from this, the effective tissue depth, a measure of the depth in the tissue, is obtained in the measurement.

The purposes in the dependent process claim represents an advantageous embodiment, if the signal $S_1$ or $S_2$ is measured twice via two identical sensors, then instead of a single value, a corresponding mean value of these two signals can be used for the further calculation.

A measuring device for determining, according to the method of a tissue equivalent radiation dose has at least two sensors with energy dependency of the detection sensitives for ionizing radiation deviating from one another.

By a sensor, a component is to be understood which has a physical, chemical or technical characteristic varying with radiation and in which this change is a measure for the radiation dose characterized by this radiation. The change is characterized by a continuous change in the physical, chemical or technical characteristic with increasing radiation dose.

Examples of such components are micro-optical or fiberoptic sensors (for example from DE 39 29 294 A1 or DE 32 34 900 A1). A micro-optical sensor is understood to be a sensor of a size less than 1 mm. Examples of such changes are the changes of optical characteristics like induced damping, scintillation, fluorescence known from DE 3929294 A1. According to DE 3929294 A1, sensors are connected via fiberoptic, radiation resistant transmission lines or fibers with a measuring and evaluation electronic circuit. The measured signals are indicated via the electronics. When the sensors are micromechanical sensors, each individual sensor can be arranged in a lumen of a multilumen catheter. Two sensors show an energy dependency of the detection sensitivity for ionizing radiation deviating from one another when their measurement signals vary differently. This difference can be determined by the type of construction, for example, by a different effective atomic number with optical sensors or as a consequence of different shielding of the sensors. In an advantageous embodiment, the measuring device is constructed to be rotationally symmetrical with reference to its sensors and is comprised of at least three sensors of which at least two show the same energy dependency of the detection sensitivity for ionizing radiation.

If two sensors are constructed identically, e.g. are optical sensors with the same effective atomic weight, the sensors show the same energy dependency of the detection sensitivity and differences of the measured signals, which are in the realm of measurement precision or are determined by the production techniques, are not significant. The rotational symmetry is with reference to the central axis of the structure along which the sensors are introduced, for example, into a tissue. Because of the rotationally symmetrical construction, the device is not sensitive to a rotation about this central axis.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
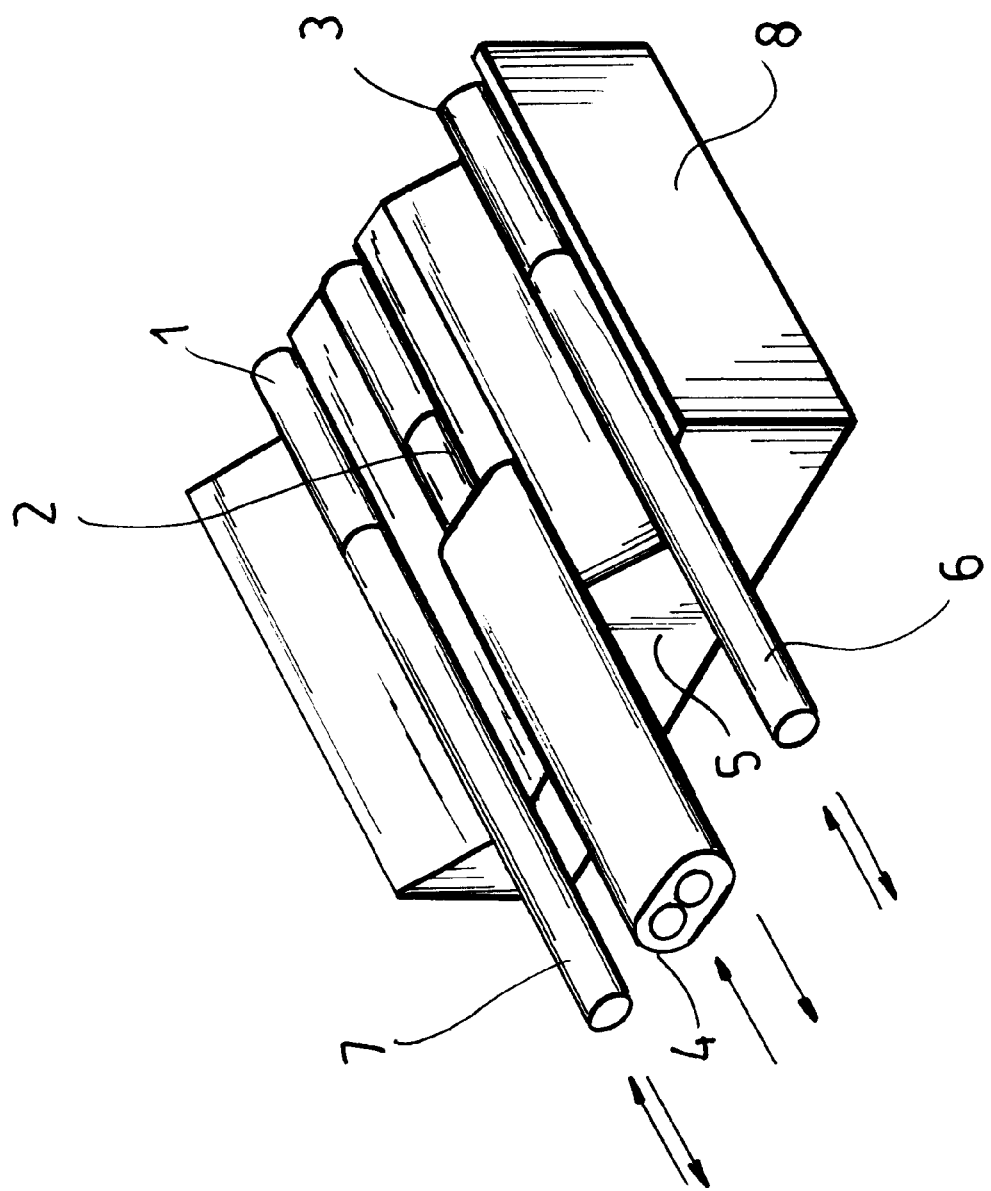
FIG. 1 is a perspective view of a planar support element for coupling to a plurality of fiberoptical radiation sensitive sensors.

FIG. 1 shows a rotationally symmetrical sensor with three radiation sensing sensor fibers 1, 2 and 3. The middle sensor fiber 2 is comprised of a PbO fiber with 60% by weight lead oxide. This is coupled to a radiation insensitive twin fiber 4 comprised of two quartz fibers (hard clad fiber with a high numerical aperture) in a common sheath 5.

The sensor fibers 1 and 3 are Ge-P doped gradient index fiber (germanium about 26% by weight, phosphorous approximately 4% by weight), which are spliced to the commercial radiation-hard communication fibers 6 and 7 (e.g. AT&T—Rad Hard 3A). The sensor fibers 1, 2 and 3 are embedded rotationally symmetrical to the longitudinal axis of the central fiber 2 in the planar substrate 8. The substrate 8 is comprised of metal, glass or silicon. Overall the planar construction is about 0.9 mm wide.

The twin fiber is used as a transmission fiber to avoid detrimental Fresnel reflections upon reading of the radiation induced light weakening. The rotationally symmetrical arrangement of the sensors makes the measuring device insensitive to a rotation about the longitudinal axis of the center sensor 2 in the radiation field. The use of two germanium-phosphorous sensors improve the signal-noise signal of the measurement signal upon readout of the germanium-phosphorous sensors 1 and 3. If the sensor fibers 1, 2 and 3 are irradiated, the light damping increases in the sensor fibers with increasing dosage. The damping is as a consequence a measure of the radiation dosage.

The dependency between damping and dosage in PbO fibers differs from the dependency of the Ge-P doped fibers 1 and 3 because of the difference in effective atomic number.

The ends of the sensors are mirrored which lie opposite the ends coupled to the transmission fibers 4, 6 and 7. The mirroring serves for light reflection. Light is emitted from the measuring and evaluating circuitry via the transmission fibers 4, 6 and 7 into the sensors. The light is reflected at the mirrored ends and thus returned to the electronic circuitry. The travel direction of the light is indicated in FIG. 1 by the 6 parallel arrows (ahead of the transmission lines). The electronic circuitry registers the change in damping and indicates the variation in the latter as a measure of the dosage.

Figure 2:
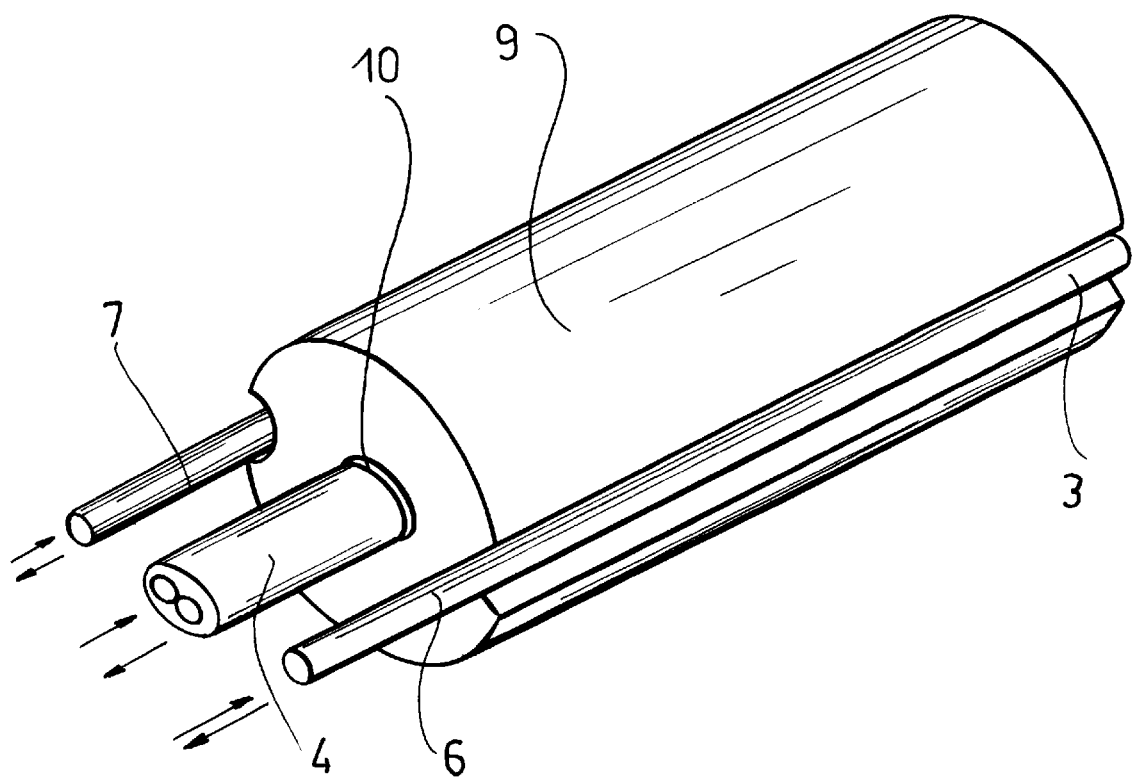
FIG. 2 is a perspective view of a metal capillary as support element for the coupling to fiberoptic radiation sensitive sensors.
Figure 3:
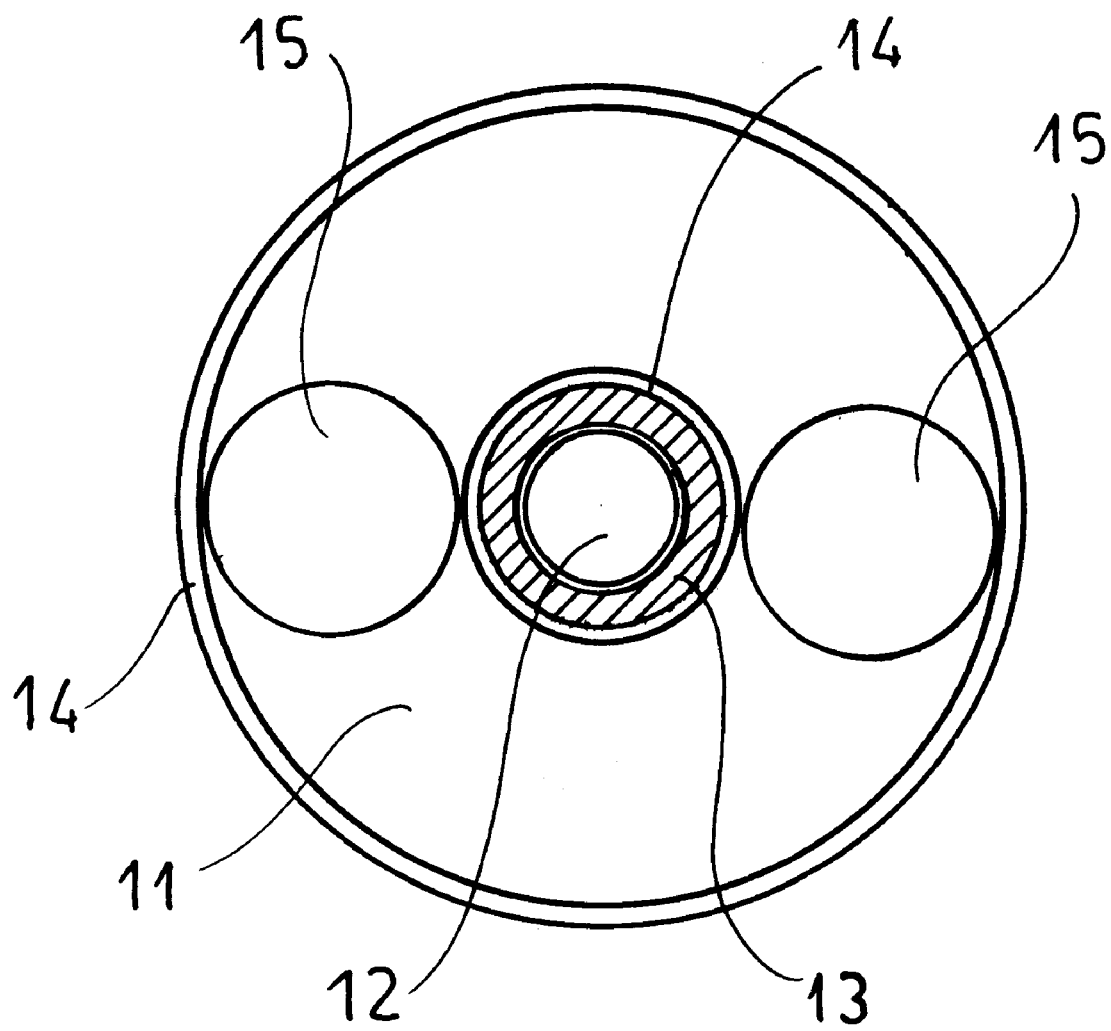
FIG. 3 is a cross sectional view of a construction with a scintillating and a radiation induced damping measure measuring fiber optic sensors.

FIG. 2 shows in principle a construction as in FIG. 1. The single difference is an embedding of the sensors in the vinyl (VA) capillary 9 instead of the planar substrate of FIG. 1. The twin fiber is fixed with epoxy cement 10. The construction shown in cross section in FIG. 3 is comprised of a scintillating NaI crystal 11 as the first sensor and a PbO fiber 12 as the second sensor. The NaI crystal 11 serves simultaneously as a support element for the PbO fibers which surround the vinyl capillary 13. To increase the light yield of the scintillating element, the end surfaces are mirrored and its inner and outer peripheral surface 14 are coated with a light scattering material absorption, e.g. barium sulfate or titanium oxide. The coupling out of light from the scintillating sensor is effected through one or more windows 15 ahead of which light waveguides are fixed. The coupling to the PbO sensors is effected once again by means of a twin fiber.

Figure 4:
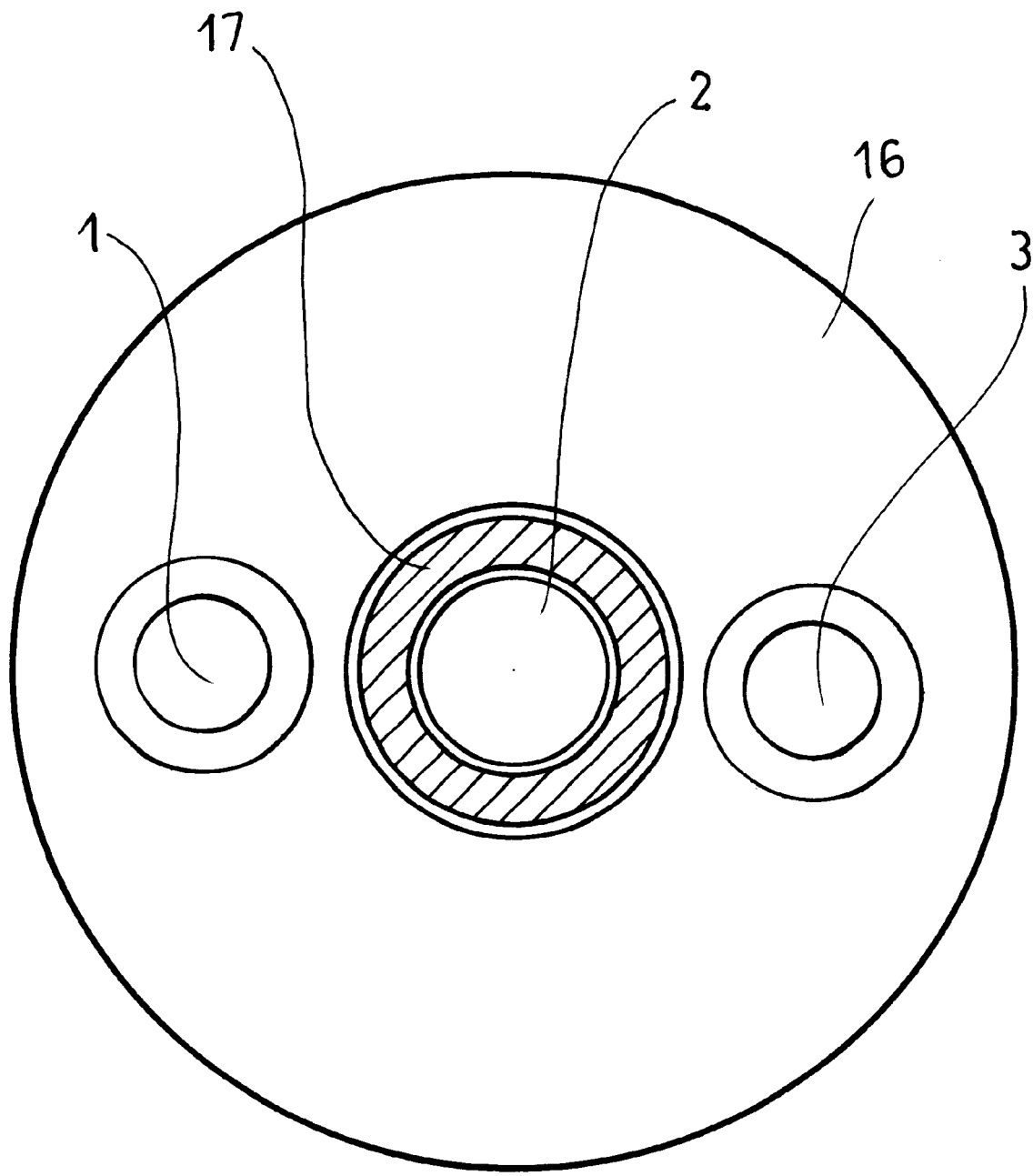
FIG. 4 is a cross sectional view of radiation sensitive sensors in a multilumen catheter.

FIG. 4 shows a construction analogous to FIGS. 1 and 2. Here, however, a three-lumen catheter tube 16 is used and is shown in cross section, for positioning the sensors 1, 2 and 3. The PbO fiber 2 is sheathed by a steel capillary 17. The steel capillary 17 serves for coupling to it a twin fiber.

Figure 5A:
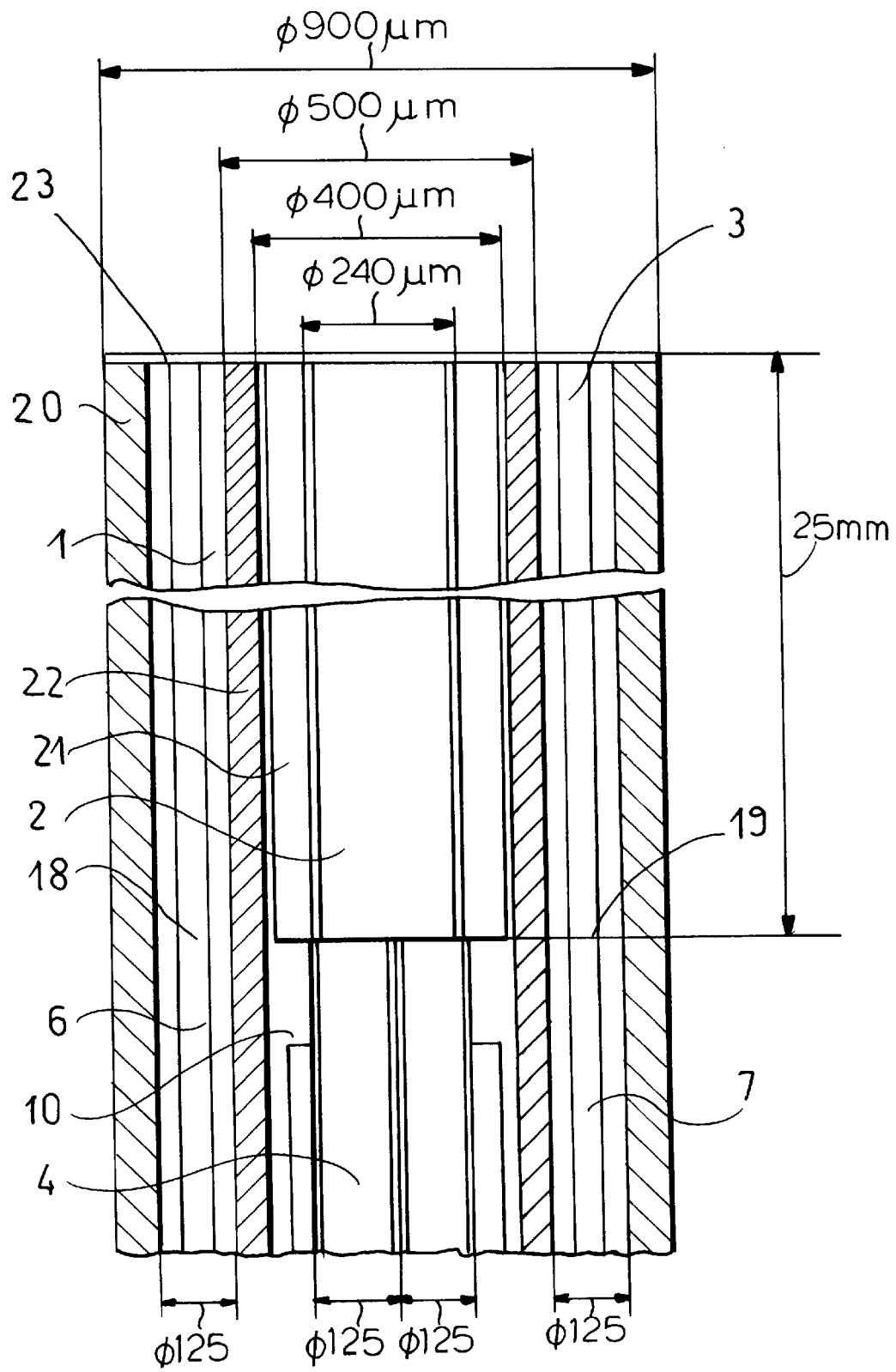
FIGS. 5a and 5b are a longitudinal section a cross section, respectively, of a construction with three radiation sensitive sensors.
Figure 5B:
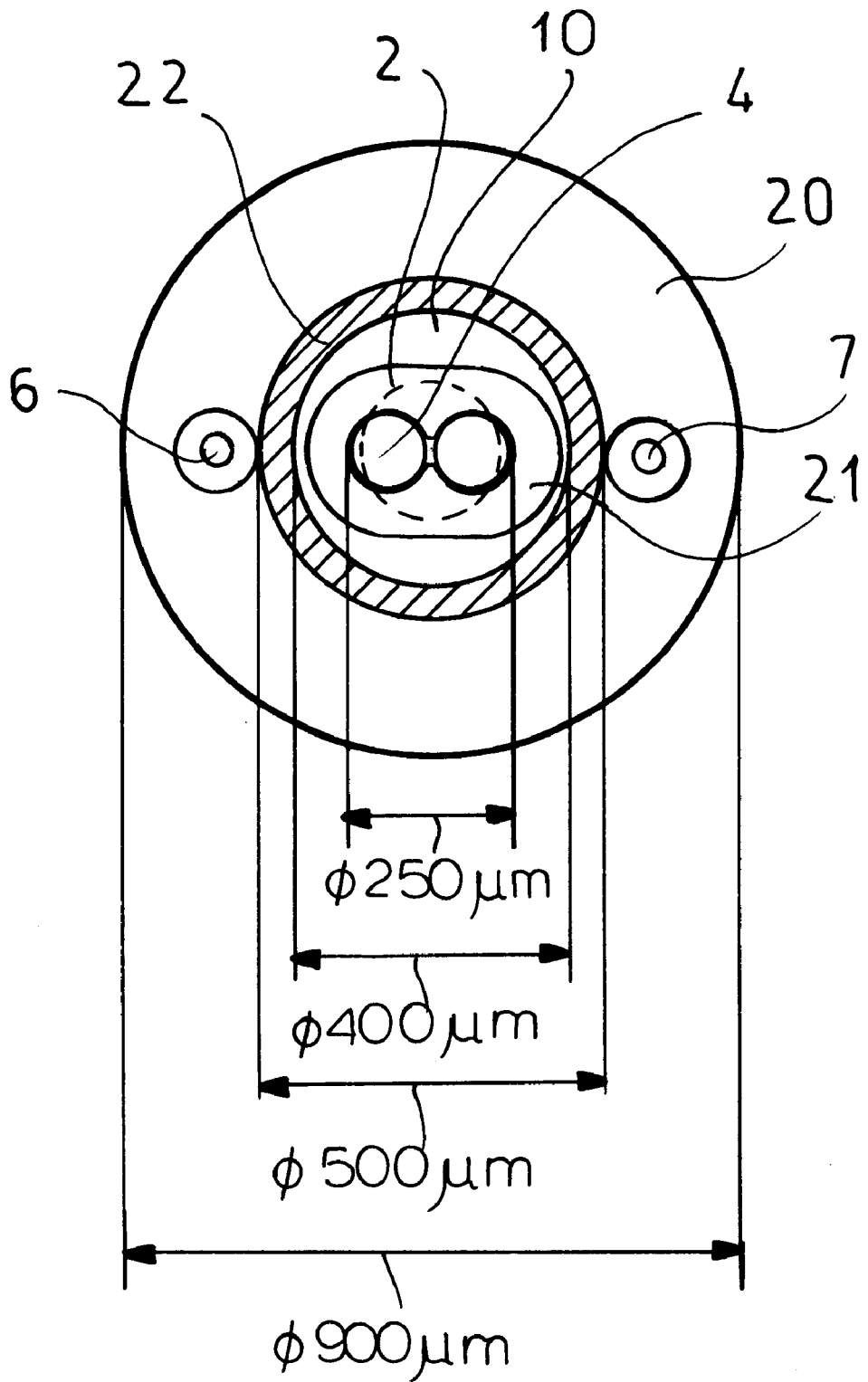

In FIGS. 5a and 5b, a further embodiment with three sensors 1, 2 and 3 analogous to those of FIGS. 1, 2 or 3 has been shown in longitudinal section (FIG. 5a) and in transverse section (FIG. 5b). The Ge-P doped gradient index fibers 1 and 3 are spliced at the locations 18 and 19 to Rad hard transmission fibers 6 and 7 and are protected by the biocompatible plotting mass 20. The PbO fiber 2 is initially encased with a sheath 21 and then with a metal capillary 22. The aluminum mirror 23 serves, as has been explained, for light reflection.

Figure 6:
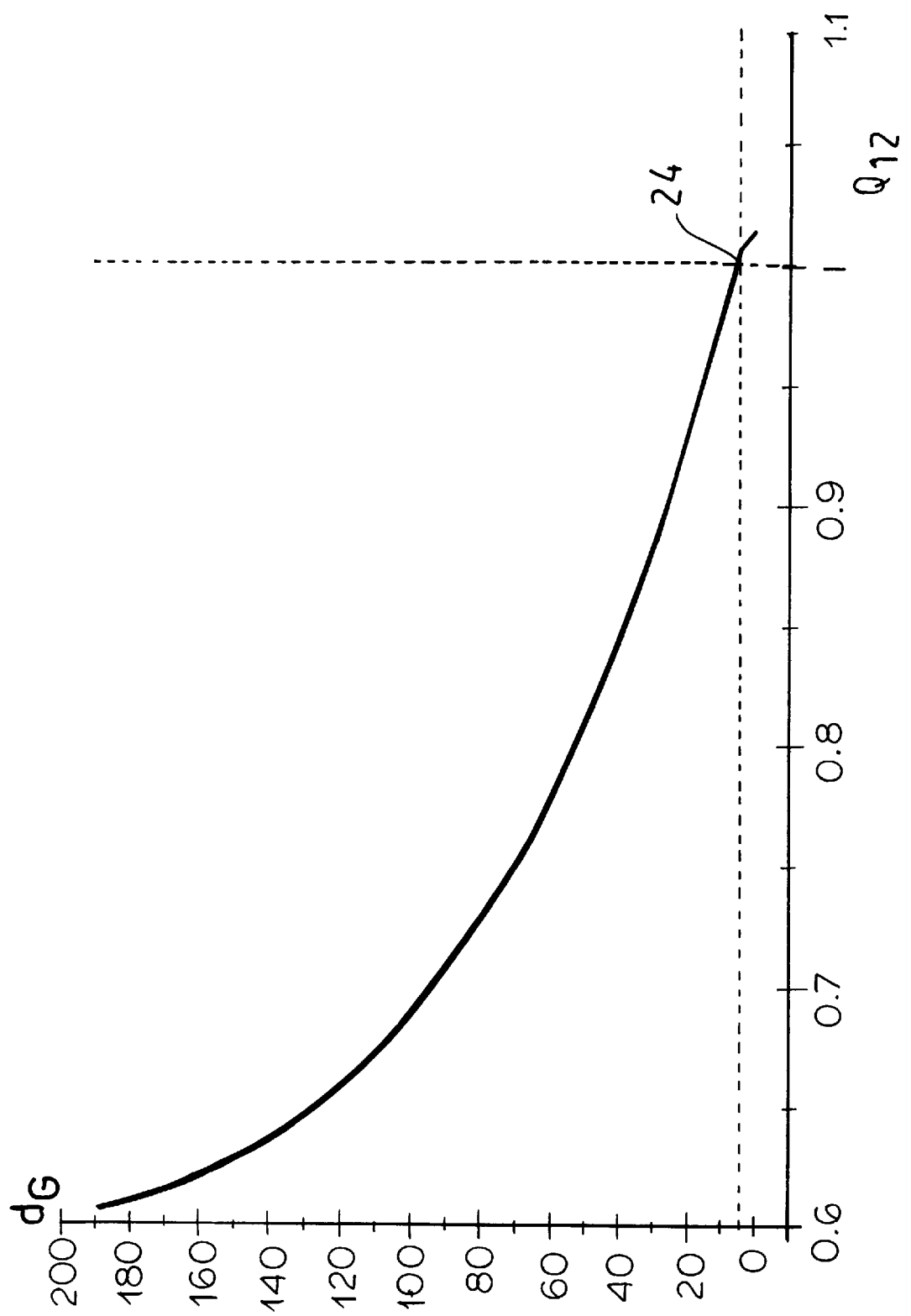
FIG. 6 is a graph of effective tissue depth as a function of the ratio of the signals of two sensors with different effective atomic numbers.
Figure 7:
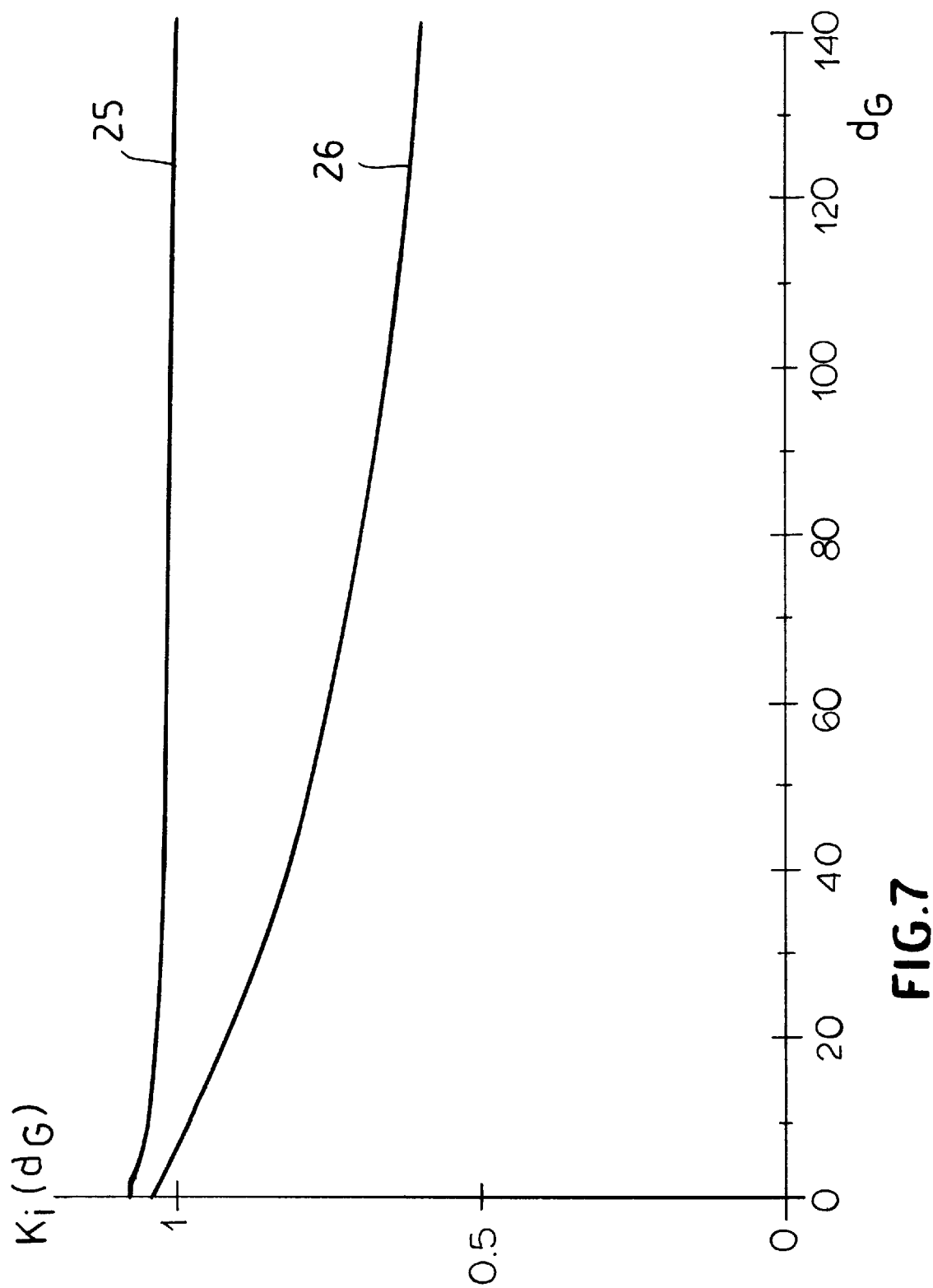
FIG. 7 is a graph of the dependency of the calibration factors of two sensors with different effective atomic numbers upon the effective tissue depths.
Figure 8:
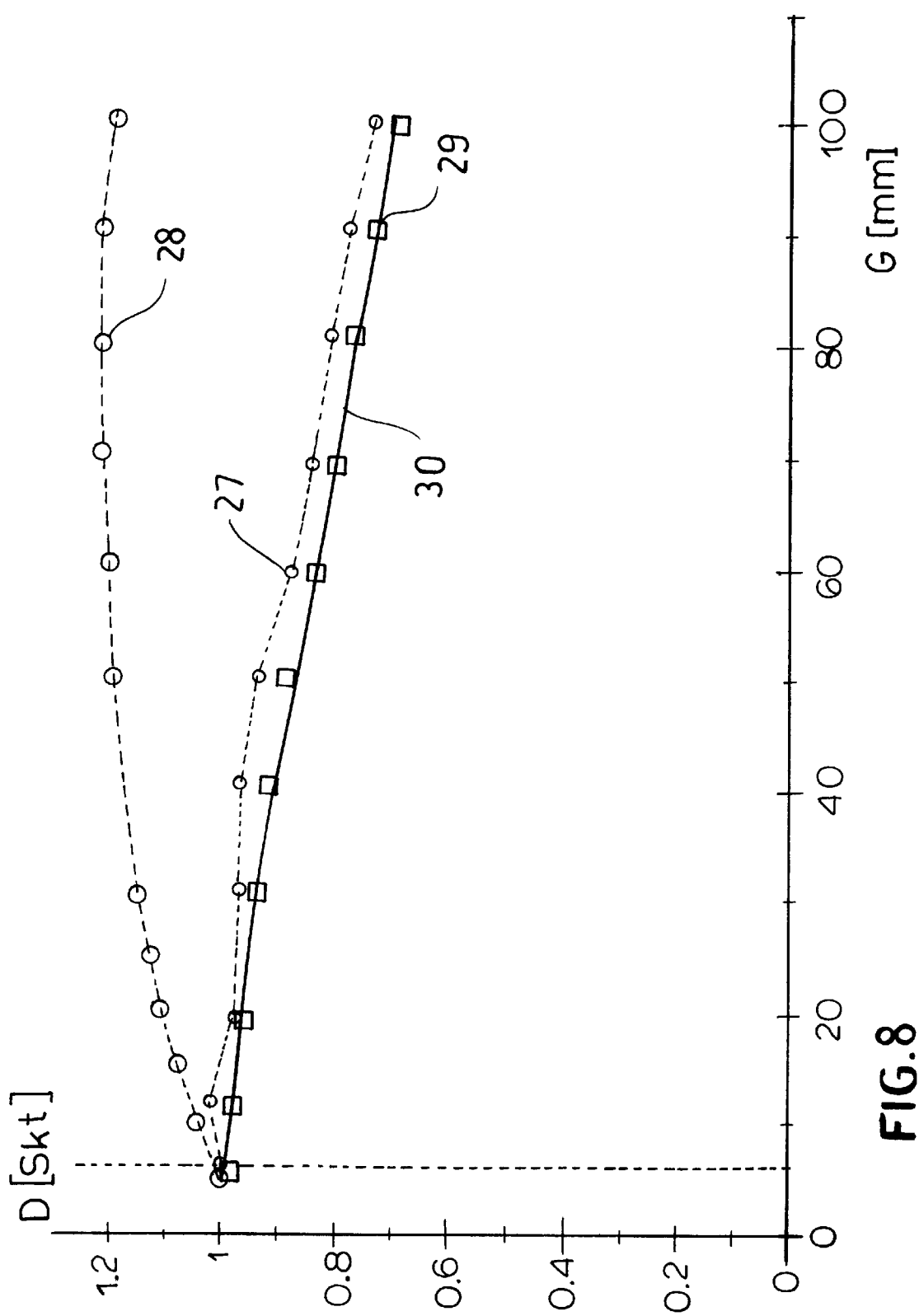
FIG. 8 is a graph of dose measurement as a function of tissue depth.

The process according to the invention can be carried out with all of the illustrated sensors. The measurement results shown in FIGS. 6, 7 and 8 are obtained with the construction according to FIGS. 5a and 5b. The tissue equivalent dose was obtained according to the description of the process.

FIG. 6 shows the effective tissue depth $d_g$ as a function of the quotient $Q_{12}$ of the 2 dose indicators $S_1$ and $S_2$ when the double sensor is calibrated at the dose maximum of the depth-dose distribution. The one signal $S_1$ represents the mean of the signals from the Ge-P sensors 1 and 3. The calibration point is found at the intersection 24 of the dotted lines.

In FIG. 7, the dependency of the calibration factor $K_i(d_g)$ of the sensors 1 and 2 has been shown with different effective atomic weights of the effective tissue depth (i=1,2). Curve 25 is obtained with sensor 1 and curve 26 is obtained with sensor 2.

FIG. 8 shows depth dose measurements with the Ge-P sensor 1 (circular point 27) as well as with the PbO sensor (circle 28) upon a radiation with CO60 energy. Displayed is the dosage D (Skt=Scale Parts) vs. the geometric tissue depth G (mm=millimeter). The vertical dotted lines characterize the depth in the calibration. Ge-P sensors and PbO sensors show an energy dependency deviating from one another of the detection sensitivity for ionizing radiation which are apparent from the measurements points 27 deviating from one another by comparison with the measurement points 28. The squares 29 show the results obtained according to the invention. A comparison of the obtained results 29 with the dosage indication of an ionization chamber shown by means of the continuous line 30, indicates that the process supplies on approximately tissue equivalent result and is substantially as precise as the PbO sensor measured result.

We claim:

1. A process for the in-vivo determination of a tissue equivalent dose in radiation therapy, comprising the steps of:
    (a) providing two optic sensors having different effective atomic numbers, characteristics which vary upon being subjected to ionizing radiation and fiberoptic outputs;
    (b) positioning both of said optic sensors close to one another in tissue of a living organism in which a tissue equivalent dose is to be measured and obtaining simultaneous measured signals $S_1$ and $S_2$ from the respective sensors;
    (c) forming a quotient $Q_{12}=S_1/S_2$ from said measured signals;
    (d) determining an effective tissue depth $d_g$ from the quotient $Q_{12}$ based upon a calibration curve having experimentally obtained calibration factors $K_1(d_g)$ and $K_2(d_g)$ depending upon the tissue depth $d_g$; and
    (e) calculating the tissue equivalent dose D according to $D=\{_1(d_g)*S_1+K_2(d_g)*S_2\}/2$.

2. The process defined in claim 1 wherein said measured signals are simultaneously from two micro-optic sensors.

3. The process defined in claim 1 wherein said measured signals are simultaneously from two fiberoptic sensors.

* * * * *